(12) United States Patent
Dubois (10) Patent No.: US 6,224,026 B1
(45) Date of Patent: May 1, 2001

(54) OVERHEAD ARTICULATED SUPPORT FOR THE HUMAN ARM

(76) Inventor: Constant Dubois, 9, rue Boucher, Hull Quebec J8Y 6G2 (CA)

( * ) Notice: Subject to any disclaimer, the term of this patent is extended or adjusted under 35 U.S.C. 154(b) by 0 days.

(21) Appl. No.: 09/304,960

(22) Filed: May 5, 1999

(51) Int. Cl.⁷ .............................. B43L 15/00; A47F 5/00; A47F 7/00; F16M 11/00
(52) U.S. Cl. ................................. 248/118.3; 248/125.2; 248/125.1
(58) Field of Search ................................. 248/118, 118.1, 248/118.2, 118.3, 125.1, 125.2; 242/381, 381.6, 379.2; 5/600, 611, 612, 616, 641, 623, 624; 128/878

(56) References Cited

U.S. PATENT DOCUMENTS

| | | | |
|---|---|---|---|
| 649,901 | * 5/1900 | Brennan | 248/118 |
| 1,000,045 | * 8/1911 | Spicer | 248/118 |
| 1,516,795 | * 11/1924 | Schwarting | 248/118 |
| 4,241,891 | 12/1980 | Rudolph | 248/123 |
| 4,390,011 | * 6/1983 | Evans | 248/118 |
| 4,548,374 | 10/1985 | Thompson et al. | 248/123 |
| 4,565,011 | * 1/1986 | Karger | 242/107 |
| 5,074,501 | 12/1991 | Hölttä | 248/122 |
| 5,279,486 | 1/1994 | Harmon | 248/122 |
| 5,348,014 | 9/1994 | Okado | 128/660 |
| 5,385,322 | * 1/1995 | Kim et al. | 248/118 |
| 5,762,282 | * 6/1998 | Wolner | 242/381 |
| 5,902,164 | * 5/1999 | Shoemaker | 242/379.2 |
| 6,042,064 | * 3/2000 | Hong | 248/118 |
| 6,086,024 | * 7/2000 | Congress | 248/118 |

* cited by examiner

Primary Examiner—Ramon O. Ramirez
Assistant Examiner—J. DeLuca
(74) Attorney, Agent, or Firm—Goudreau Gage Dubuc (57) ABSTRACT

A system for supporting a user's arm, comprises an armrest. The armrest is suspended and supported from a horizontally movable structure comprising a vertically movable member through which the armrest is suspended, a counterbalancing return-force producing assembly connected to the vertically movable member to counterbalance at least in part the weight of the user's arm, and a movement-resisting assembly connected to the vertically movable member to resist to vertical movement of the vertically movable member. According to a preferred embodiment, the vertically movable member comprises a cable, the counterbalancing return-force producing assembly comprises a first, spring-loaded reel, and the movement-resisting assembly comprises a second reel on which turns of the cable are wound and provided with at least one lateral face, and at least one friction disk applied to the lateral face of the second reel to resist to vertical movement of the wire. The present invention is also concerned with a specific embodiment of the armrest.

16 Claims, 6 Drawing Sheets

OVERHEAD ARTICULATED SUPPORT FOR THE HUMAN ARM

BACKGROUND OF THE INVENTION

1. Field of the Invention

The present invention relates to an ergonomic apparatus for supporting the human arm during manual operations so as to counterbalance at least a part of its weight and reduce the strain on supporting muscles and tendons.

More specifically, the invention is particularly, although not exclusively intended for ultrasonic diagnostic operations and aims at providing a simple, esthetical and practical solution to the increasing problem of fatigue and pain caused to operators by the repetitive manipulation of the ultrasonic probe in a position where the operator's arm is usually extended far from his body, thus causing a high solicitation at the biceps and shoulder level. Effectively, many current medical applications of ultrasonic diagnostic, such as in obstetrics, require intensive manipulation of the probe around the patient's tissues and obstacles to obtain images as good as possible or track moving targets. Therefore, operators' arms are much solicited causing pain, disease, low productivity, absenteeism, that induce both human and economic costs.

Although the invention will be described in detail with respect to the latter field of application, it shall be understood that it might be used in many other fields such as assembly, physiotherapy and assistance to persons affected by a restriction of arm mobility.

2. Brief Description of the Prior Art

A few solutions to the problem of holding an ultrasonic probe have been proposed in the past and they all suffer from major drawbacks. Namely, all of them are designed to hold the probe itself and provide no assistance to the operator for supporting the weight of his own arm acting in cantilever and causing an important torque to be counterbalanced by the effort of the arm and shoulder muscles and tendons. Such a mechanism is disclosed in U.S. Pat. No. 5,348,014 (Okado) issued on Sep. 20, 1994, which describes an overhead arm mechanism provided with a constant force spring counterbalanced wire to which the probe is suspended. Considering that most contemporary probes are much lighter than the operators arm, supporting the probe alone provides very limited relief of the physical stress to be supported by the operator. Even if the winding force of the wire was increased to account for the arm weight, the point of application of the compensating force would not be adequate and added stress in the wrist and no significant comfort improvement if any would yield. Moreover, that support is limited in mobility and positioning flexibility since it is fixed to the ultrasonic apparatus body and does not provide operator adjustable counterbalancing force.

U.S. Pat. No. 5,279,486 (Harmon) issued on Jan. 18, 1994 discloses a medical support using an horizontal arm to support a wire through two pulleys. One end of the wire supports a medical apparatus while a counterweight is attached to the other end of the wire and counterbalances the weight of the apparatus. That concept with limited number of degrees of freedom is only appropriate for static support of an apparatus and do not feature practical adjustment of the counterbalancing force as required for supporting the arm in different positions and providing optimal comfort to different operators.

U.S. Pat. No. 4,548,374 (Thompson et al.) and U.S. Pat. No. 4,241,891 (Rudolph) respectively issued on Oct. 22, 1985 and on Dec. 30, 1980, provide even worse solutions for supporting the probe, since the weight of most of the articulated supporting arm is balanced by a counterweight located near the base. These concepts result in sturdy and heavy structures which present a high level of friction and inertia that would prevent utilisation as a human arm support since freedom of movement would be too much affected.

Many arm supports are referenced in the prior art, but they are all intended to relief stress and pain experienced by keyboard operators. These systems, for example the system described in U.S. Pat. No. 5,074,501 (Holtta) issued on Dec. 24, 1991, support the operator's arm from underneath and provide no supported or balanced mobility over a three dimensional work envelope, and therefore would not comply with an application requiring such a level of freedom as for ultrasonic diagnostic apparatus operators, assembly tasks, restrained mobility persons or like applications.

OBJECTS OF THE INVENTION

The present invention provides an overhead articulated support for the human arm which overcomes the limitations and drawbacks of the above mentioned solutions of the prior art, and more specifically:

a first object of the instant invention is to provide an arm support that counterbalances at least a part of the weight of the arm of a person and follows its movement rather than guiding it within a three-dimensional working envelope, thus causing a minimal restriction to the movements, preserving the full mobility of the hand and wrist of the user and giving a general impression of flotation;

a second object of the present invention is to provide a discrete and safe support for the human arm in which the arm is supported from overhead to avoid the presence of obstacles within the working envelope or the line of sight of the user and eventual patient, collaborator or other persons, and to prevent people from running into a part of the support and get injured;

a third object of the present invention is to provide a support which features fast and simple user settable adjustments over a wide range of values for the counterbalancing force and the position of the arm rest to match the personal physical characteristics of any user;

a fourth object of the present invention is to provide an arm support in which the counterbalancing force is substantially linear over the entire vertical stroke:

a fifth object of the present invention is to provide an arm support that is mobile, compact, collapsible and requires very low space for storage when not in use;

a sixth object of the present invention is to provide an arm support featuring an adjustable friction device to partially or totally lock the position of the vertical axis or reduce the effect of the relief force in one or both directions;

another object of the instant invention is to provide an arm support incorporating a fixed supporting ring to hold the probe cable from a vertical point and thus relief the stress its weight normally causes on the operator's wrist;

a further object of the present invention is to provide an arm support that comprises a minimum number of parts, requires almost no maintenance, is esthetical and is economical to produce; and a still further object of the present invention is to provide an arm support that comprises an armrest that is self adjustable in order to automatically wrap around the user's arm and firmly adhere to it when a downward pressure is exerted by the arm, and substantially release the arm when the latter is moved vertically with respect to the armrest.

SUMMARY OF THE INVENTION

More specifically, in accordance with the invention as broadly claimed, there is provided an overhead articulated support for the human arm, comprising an armrest suspending structure comprising:

a vertically movable member through which the armrest is suspended;

a counterbalancing return-force producing assembly connected to the vertically movable member to counterbalance at least in part the weight of the users arm; and a movement-resisting assembly connected to the vertically movable member to resist to vertical movement of the vertically movable member.

In accordance with a preferred embodiment of the overhead articulated support, the vertically movable member comprises a cable, the counterbalancing return-force producing assembly comprises a first, spring-loaded reel, and the movement-resisting assembly comprises a second reel on which turns of the cable are wound and comprising at least one lateral face, and at least one friction disk applied to the lateral face of the second reel to resist to vertical movement of the wire.

Preferably, the cable is a substantially rigid cable whereby (a) the second reel is rotated as the cable is pulled downwardly to induce resistance to downward movement of the cable, and (b) the substantially rigid cable looses frictional contact with the second reel when no downward pulling force is applied to the substantially rigid cable to enable upward movement of this cable and rewinding thereof on the first reel substantially without resistance.

In accordance with another preferred embodiment;
the vertically movable member comprises a wire;
the counterbalancing return-force producing assembly comprises an elastic member having a first end fixedly connected to the horizontally movable structure and a second end, a first set of laterally adjacent pulleys rotatively mounted on an axle itself fixedly mounted on the horizontally movable structure, and a second set of laterally adjacent rotative pulleys between the first set of pulleys and the second end of the elastic member, wherein the wire has a first end attached to the second end of the elastic member, is successively passed through the pulleys of the first and second sets to form a plurality of loops, and has finally its second end attached to the armrest; and the second end of the wire is attached to the armrest through a generally vertical rod slidably mounted in a generally vertical tube of the horizontally movable structure and the movement-resisting assembly comprises a friction element interposed between the generally vertical rod and the generally vertical tube.

The present invention also relates to a system for supporting a user's arm, comprising:

an armrest for receiving the users arm;

a horizontally movable structure for suspending and supporting the armrest, comprising: a vertically movable member through which the armrest is suspended; a counterbalancing return-force producing assembly connected to the vertically movable member to counterbalance at least in part the weight of the users arm; and a movement-resisting assembly connected to the vertically movable member to resist to vertical movement of the vertically movable member.

According to a preferred embodiment of the system, the horizontally movable structure further comprises a base member with a generally vertical tube, a generally vertical post slidably mounted in the generally vertical tube of the base member, a first arm pivotally mounted on the generally vertical post about a generally vertical pivot to move in a generally horizontal plane, and a second arm pivotally mounted on the first arm about a generally vertical pivot to move in a generally horizontal plane, wherein the armrest is suspended from the second arm.

Further in accordance with the present invention, there is provided an armrest for supporting a user's arm, comprising a C-shaped shell having first and second ends, a lever pivotally mounted at the first end of the C-shaped shell and pivoting on the first end to close the C-shaped shell, and a flexible band having a first end attached to the lever and a second end attached to the second and of the C-shaped shell. In operation, when the user's arm is placed on the flexible band, the lever is pulled and pivoted to close the C-shaped shell and surround the users arm with the flexible band.

Soft padding material can be disposed between the C-shaped shell and the flexible band, and the first end of the flexible band is preferably formed with a pocket to receive the lever.

Advantageously, the armrest further comprises a connecting rod through which said armrest is suspended, and a pivotal mechanism for connecting the C-shaped shell to the connecting rod, this pivotal mechanism defining a rotation axis and comprising a rotation-limiting arrangement.

The objects, advantages and other features of the present invention will become more apparent upon reading of the following non restrictive description of preferred embodiments thereof given by way of example only with reference to the accompanying drawings.

DETAILED DESCRIPTION OF THE PREFERRED EMBODIMENTS

Preferred embodiments of the overhead articulated arm support according to the present invention will now be described in connection with the appended drawings.

Figure 1:
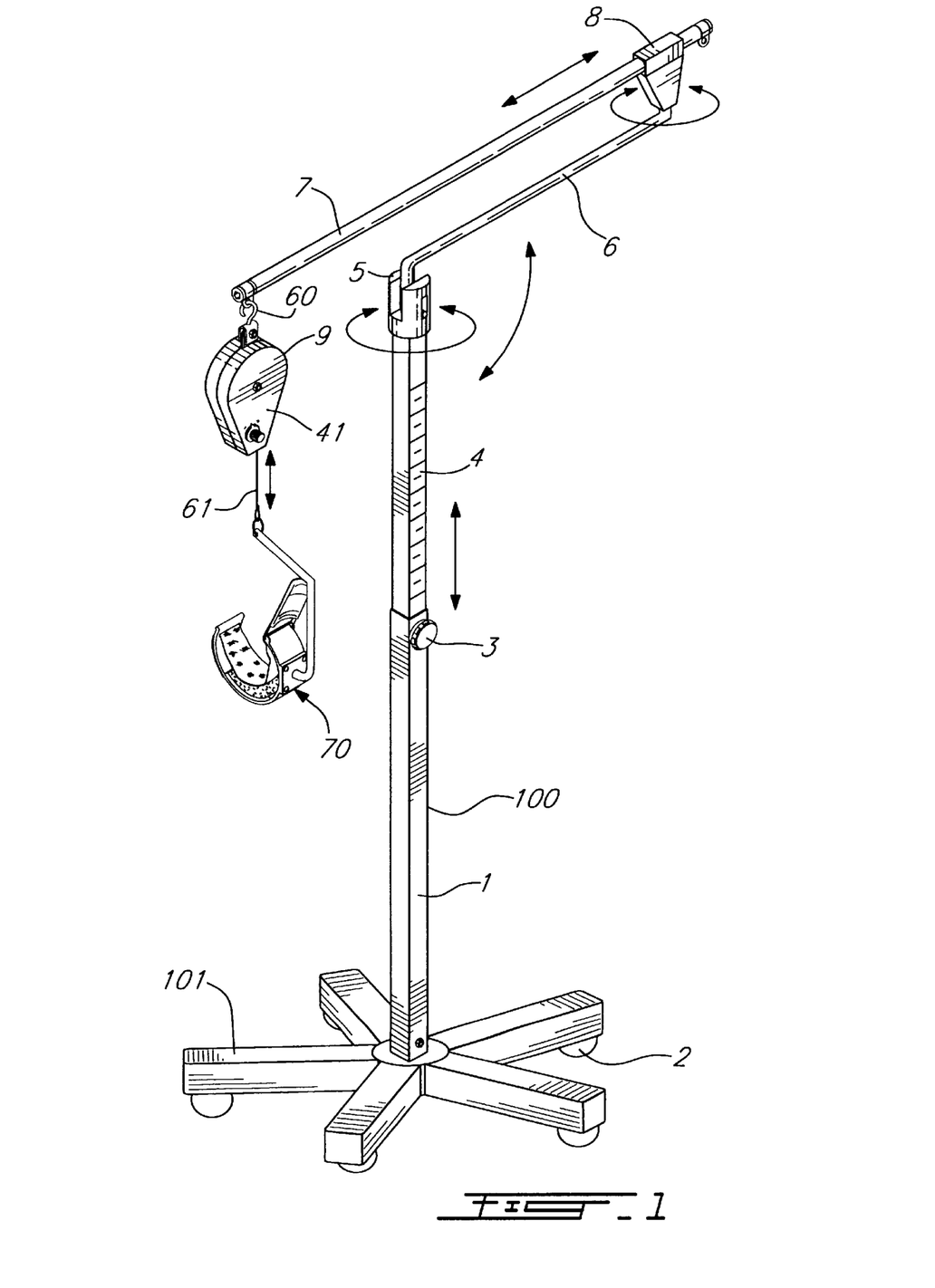
FIG. 1 is an isometric view of an overhead articulated arm support according to the present invention, including an armrest.
Figure 3:
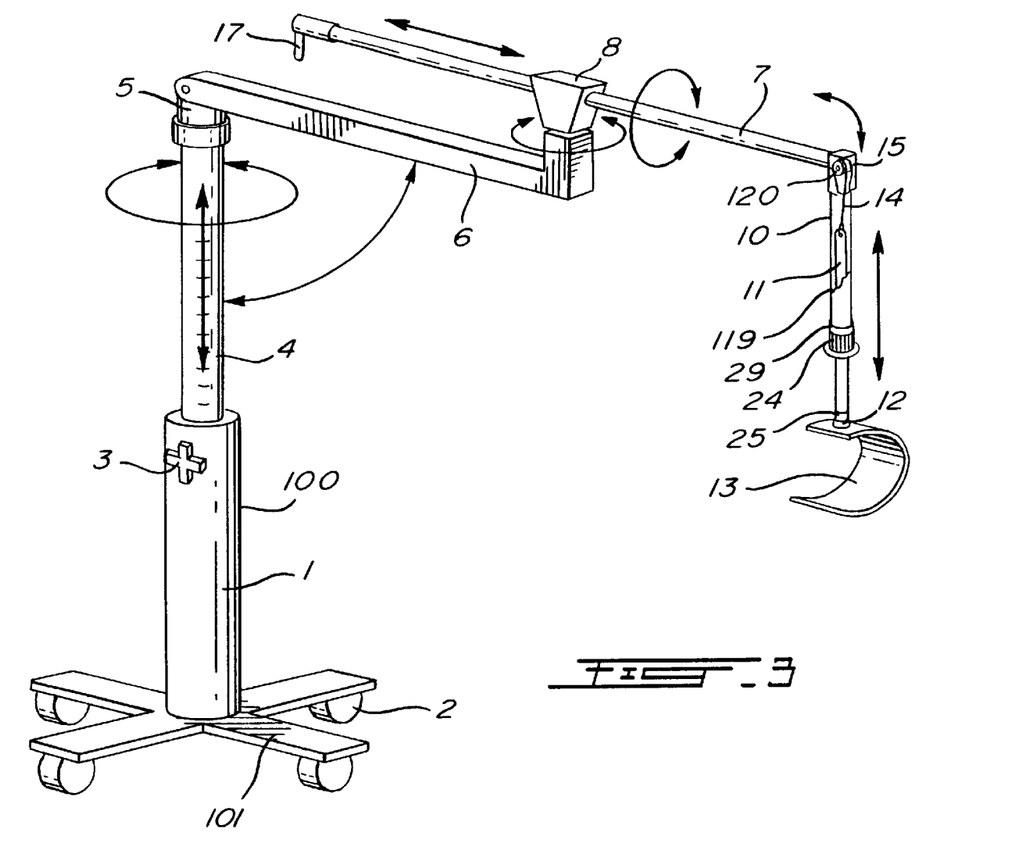
FIG. 3 is an isometric view of an overhead articulated arm support in accordance with the present invention, including an ultrasonic probe and cable.

Referring to FIGS. 1 and 3, the overhead articulated support for the human arm comprises a base assembly 1 provided with a set of radially and horizontally extending legs such as 101 each having a free end provided with a locking roller 2. From the center of the set of radially and horizontally extending legs 101 extends a vertical tube 100 provided with a height adjustment knob 3. A graduated post 4 with reference numerals (not shown) is slidably inserted in the vertical tube 100 and locked at the desired height through knob 3. A main arm member 6 has a proximal end pivotally mounted on a rotary joint 5 mounted on the upper end of graduated post 4. In the operating position of FIGS. 1 and 3, rotary joint 5 allows the main arm member 6 to pivot about a vertical axis in a horizontal plane over 360°. Also, the rotary joint 5 enables the main arm member to unfold 90° upright to take less space for storage. During storage, post 4 can also be retracted to hide almost completely in tube 100. A sliding arm member 7 slides in a self lubricated pushing inside a generally horizontal bore provided in a "T" connector 8 itself rotatably mounted on the distal end of main arm member 6 to permit rotation of the sliding arm member 7 over 360° about a vertical axis in a horizontal plane. The sliding arm member 7 is also free to rotate in the bore about its longitudinal axis.

Figure 2:
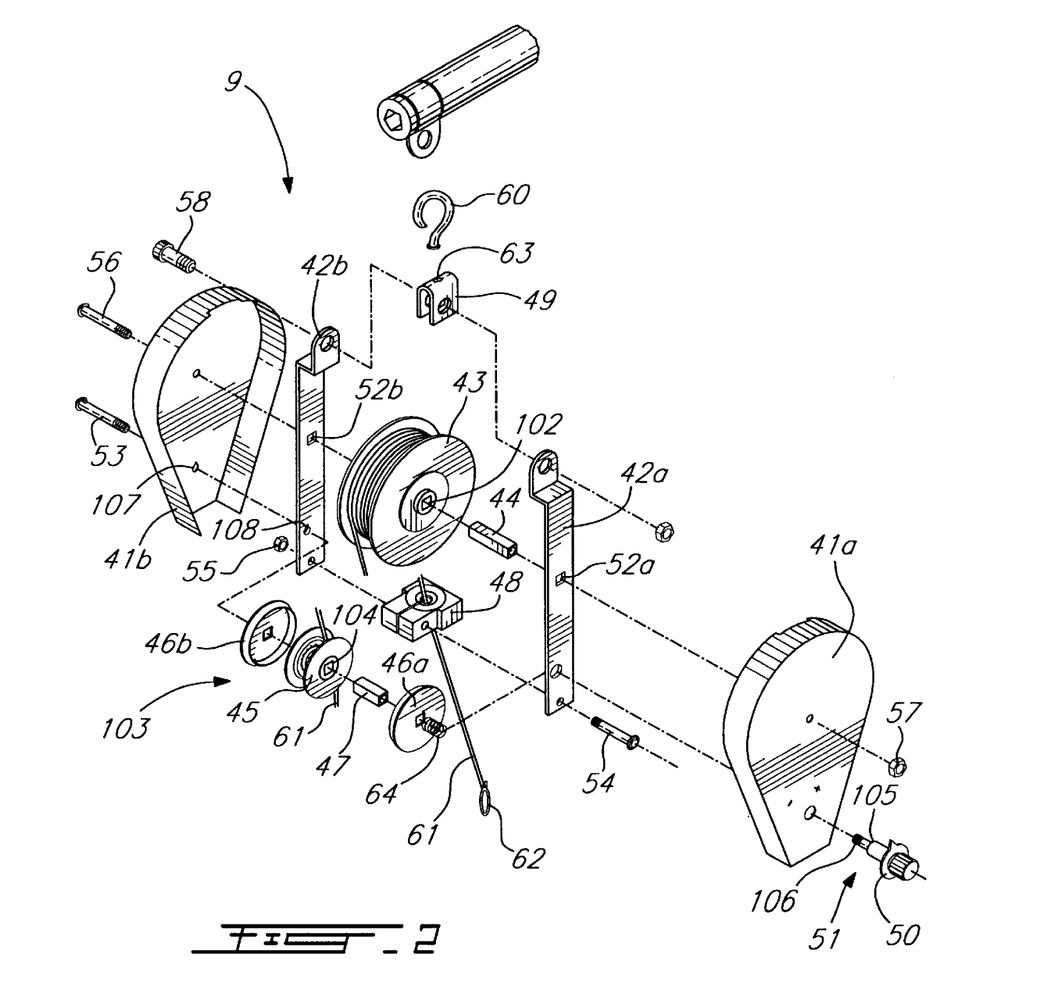
FIG. 2 is a detailed exploded view of a vertical assembly, counterbalancing device and movement-resisting assembly of the overhead articulated arm support of FIG. 1.

Referring now to the preferred embodiment of FIG. 1, a vertical assembly 9 is suspended by a hook 60 from one end of the sliding arm member 7. This vertical assembly 9 comprises a semi-flexible cable 61 preferably made of steel, emerging downwardly from a housing 41 and terminated by a loop or a quick-connect fastener 62 (FIG. 2). An armrest assembly 70 is removably connected to the loop or quick-connect fastener 62.

FIG. 2 is a detailed illustration of the vertical assembly 9 of the preferred embodiment of FIG. 1. The relatively rigid cable 61 is wound on a spring-loaded reel 43 of a type well known to those of ordinary skill in the art, provided with an inside flat spiral spring or equivalent (not shown) maintaining a substantially constant force of about three pounds when the cable 61 is pulled from the reel 43. Reel 43 is rotatively mounted on a shaft 102 having an axial opening square in cross section. The axial opening is itself mounted on a square shaft 44 assembled in the square holes 52a and 52b of support members 42a and 42b using a bolt 56 and an associated nut 57. Of course, the flat spiral spring or equivalent (not shown) is mounted inside the reel 43 and comprises one end attached to the reel 43 and another end attached to the shaft 102.

The upper portion of support members 42a and 42b are assembled together as well as with a connector 49 using bolt 58 and nut 59. A hook 60 is inserted in a hole 63 of connector 49 to support the vertical assembly 9. Cable 61 from the reel 43 passes through a guide member 48 assembled between the lower ends of the support members 42a and 42b using bolt 54 and nut 85.

At an intermediate level between the reel 43 and the guide member 48, a friction reel assembly 103 is mounted between the two supports 42 a and 42b. The friction reel assembly 103 comprises:

a friction reel 45 on which the semi-flexible cable 61 emerging from the reel 43 is wound approximately two turns before passing through the guide member 48;
a shaft 104 with an axial opening square in cross section, reel 45 being rotatively mounted on the shaft 104;
two friction disks 46a and 46b;
a square bushing 47 with inside threading;
a tension spring 64;
a tension knob 50;
a shaft 51 provided with a shoulder 105 and terminated by a threaded portion 108; and
a lock bolt 53.

These components are assembled as follows. The lock bolt 53 is inserted through a perforation 107 in a first housing portion 41b and a perforation 108 in the support member 42b for anti-rotation. Bushing 47 is tightly screwed on the bolt 53 and the friction disk 46b, the tension reel 45 (more specifically the shaft 104 on which the reel 45 is rotatively mounted) and the friction disk 46a are inserted on the bushing 47. The friction disks 46a and 46b are provided with square holes to prevent rotation of these friction plates on the bushing 47; only the reel 45 is allowed to rotate on the shaft 104. The assembly is completed by the insertion of the shaft 51 through a second housing portion 41a, the support member 42a and the tension spring 64 abutting on the face of the shoulder 105, to finally screw the threaded portion 106 inside the square threaded bushing 47. The knob 50 assembled on the shaft 51 can thus be rotated clockwise or counter-clockwise to increase or reduce the normal force between the tension reel 45 and the friction disks 46a and 46b as determined by the compression length of spring 64. The variation of the normal force provides an adjustment of the friction force produced on reel 45 by the friction disks 46a and 46b and therefor of the tension in the cable 61 when it is being pulled down. Due to the relative rigidity of the cable 61 with respect to the diameter of the tension reel 45, when the downward pulling force is released, the cable 61 loses frictional contact with the tension reel 45 and in being pulled up by the spring loaded reel 43 and rewound.

As can be seen, the two housing portions 41a and 41b are assembled together through the bolt 56 and nut 57.

In operation, the user first adjusts the lateral position and the height of the graduated post 4 on the base 1 through the knob 3 so that his (her) arm lying on the rest member 13 is floating at the desired average working height within the work envelope. The nominal horizontal distance between the base 1 and the centre of the work envelope is adjusted by manually sliding the sliding member 7 in or out.

The user's arm is supported in the armrest suspended to the free end of cable 61, is counterbalanced by an upward force equal to the friction force due to the friction reel 45 plus the pulling force of the spring loaded reel 43. If that counterbalancing force is set to be approximately equal to the weight of the users arm, at any time, the user can exert a slight downward force to move to a lower vertical position and return to a floatation-like mode. When the user moves his arm to an upper horizontal plane, the friction reel 45 has no effect and the counterbalancing force is momentarily reduced to approximately three pounds as determined by the spring loaded reel 43. This has no significant drawback in the contemplated application since the fatigue builds-up during the longer periods in a steady position.

Figure 7:
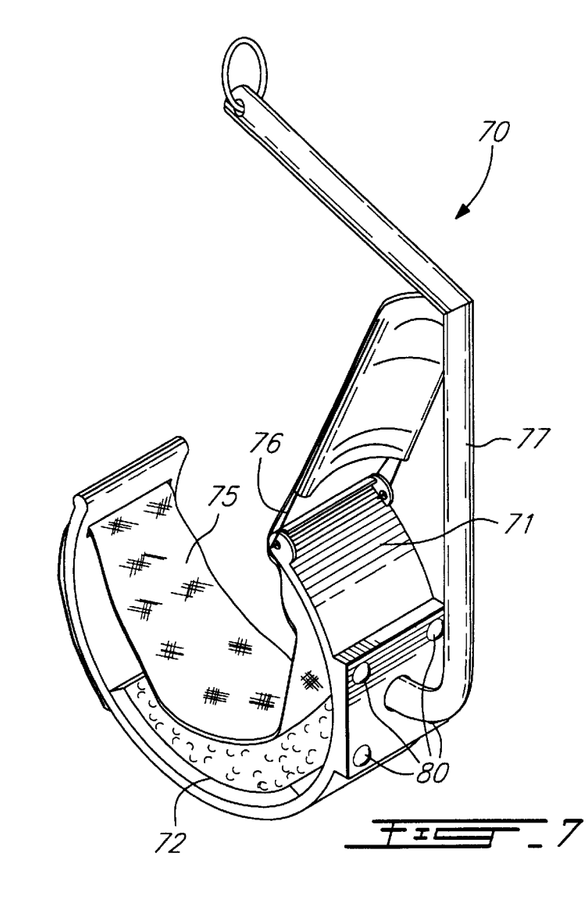
FIG. 7 is an isometric view of the armrest of the overhead articulated arm support of FIG. 1.

To ensure that the users arm is always properly supported, an armrest 70 of special construction is provided in the preferred embodiment of FIG. 1. FIG. 7 is an enlarged view of this self-adjustable armrest, while the detailed assembly is provided at FIG. 8.

Figure 8:
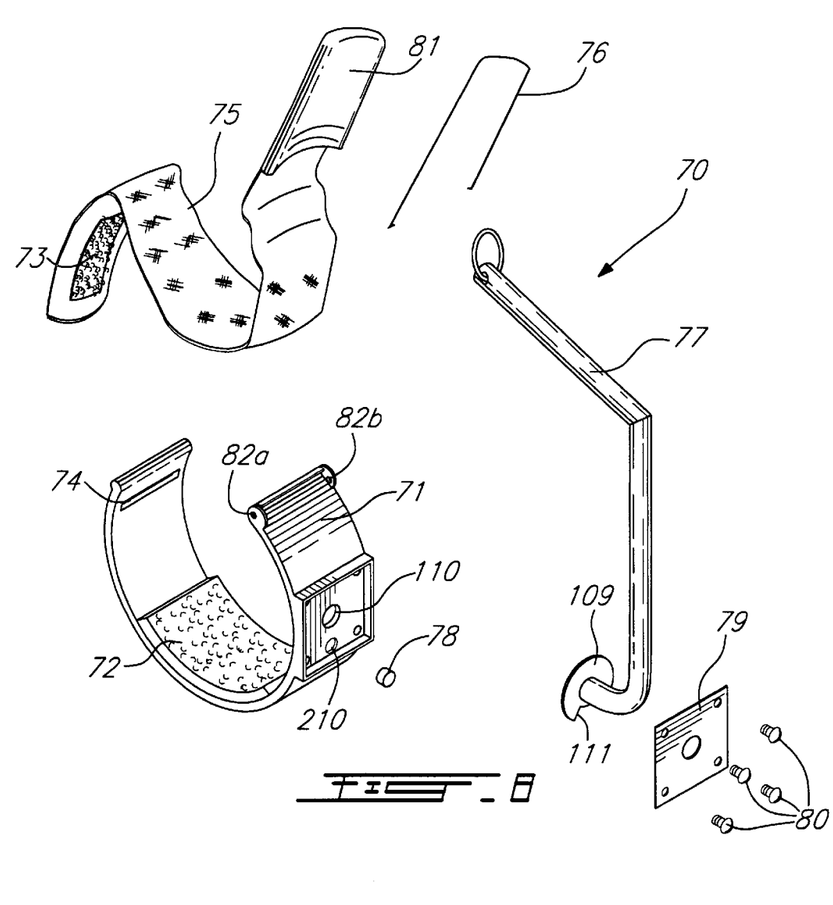
FIG. 8 is an assembly drawing of the armrest of FIG. 7.

Referring to FIGS. 7 and 8, a connecting rod 77 supporting the armrest 70 is bent in a "C" shape to provide proper balancing when connected to the vertical assembly 9 of the overhead articulated arm support. The lower end of the rod 77 comprises a notched annular flange 109 to be connected to a shell 71 of the arm rest 70 using a perforated plate 79, a pin 78 and four screws 80. As can be seen in FIG. 8, the lower end of the rod 77 protruding horizontally (not shown) from flange 109 is pivotally inserted in a hole 110 of the shell 71. Also, the pin 78 is inserted in a hole 210 of the shell 71 as well as in the notch 111 of the annular flange 109 to limit rotation of the shell 71 about the lower end of the rod 77 to the angular extent of the notch 111.

A soft pad 72 is installed inside the shell 71 to provide some cushioning. A lever 76 made of a folded steel wire is pivotally assembled to one end of the shell 71 in holes 82a and 82b. A support band of flexible anti-slip material 75 has one end terminated by a pocket 81 inserted on the lever 76 and a second end inserted through a slot 74 provided in the shell 71 at the end opposite to the holes 82a and 82b. The second end of the support band 75 comprises a strip of Velcro® material 73 for attaching this second end to a complementary strip of Velcro® material provided on the outer surface of the shell 71. These two strips of Velcro® strip enable for adjustment of the armrest 70 to the size of the user's arm.

In operation, when a user rests his arm on the support band 75, the band is pushed toward the bottom of the shell 71 to sit against the pad 72. This movement pulls down the U-shaped lever 76 covered by the pocket 81 and brings it into intimate contact with the upper part of the arm thus providing in cooperation with the support band 75a closely wrapped arrangement and a firm grip around the arm to maintain the arm solidly inside the armrest 70. When the users arm is moved upwardly with respect to the armrest 70, the lever 76 covered by pocket 81 automatically flips up and releases the arm.

FIG. 3 illustrates a second preferred embodiment of the present invention. A vertical arm assembly 119 comprises an outer tube 10 having an upper end rotatably suspended about a horizontal pivot 120 to one end of the sliding arm member 7. The vertical arm assembly 119 also comprises a rod 11 slidably mounted in the outer tube 10, rod 11 being provided at its lower end with a universal joint 12 holding an armrest 13. The upper end of rod 11 is attached to a wire 14 guided by a pulley 15 at the 90° intersection between the arm member 7 and the tube 19, the pulley 15 rotating about the horizontal pivot 120. The wire 14 has another end connected to a counterbalancing unit 121 incorporated in the sliding arm member 7, as shown in detail in FIG. 4. A stop member (flange) 24 on the rod 11 limits retraction of the rod 11 inside the tube 10.

A friction coupling assembly 29 is mounted between the tube 10 and the rod 11 to adjust a force of friction against sliding movement of the rod 11 in the tube 10 between a free sliding position and a locked position. This feature allows the user to reduce or eliminate the counterbalancing force to maintain a fixed position for a certain time or apply downward pressure as a function of the operations to be carried out.

Figure 4:
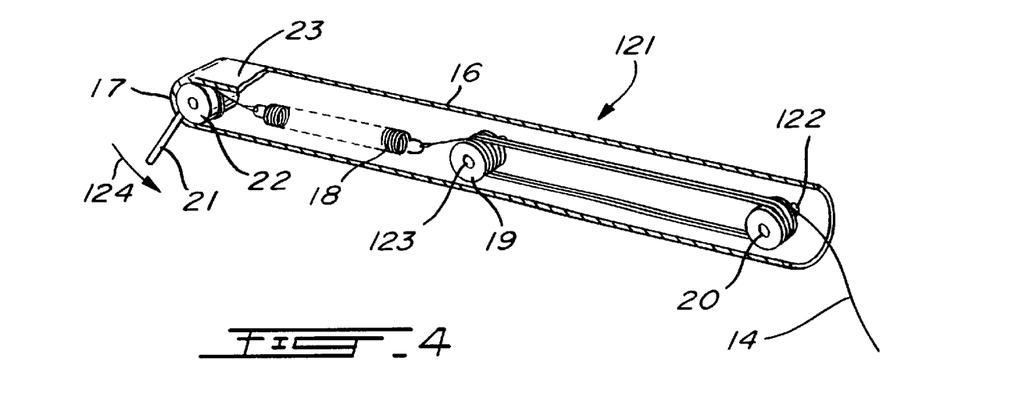
FIG. 4 is a longitudinal cut-away isometric view of sliding arm member of the overhead articulated arm support of FIG. 3.

Referring to FIG. 4 of the appended drawings, the counterbalancing unit 121 is located in a tube 16 of the sliding arm member 7. The counterbalancing unit 121 comprises a force adjustment device 17, a coil spring 18 and two sets of laterally adjacent pulleys 19 and 20. The pulleys of set 20 are rotatably mounted on an axle 122 extending across one end of the tube 16 adjacent to pulley 15. Regarding the set of pulleys 19, it is located in the proximity of the one end of the coil spring 18. Wire 14 is guided by pulley 15 and successively passes through each pulley of the sets 19 and 20 to finally connect to one end of the coil spring 18. Thw other end of the coil spring 18 is connected to the force adjustment device 17. Since the set of pulleys 19 is free to move along the longitudinal axis of the tube 16, the pulleys act as a stroke divider. The stroke of the rod 11 is transmitted to one end of the wire 14 and the pulled length splits equally in each loop between the two sets of pulleys. Hence, the spring 18 is only extended by a length equal to the stroke of the rod divided by the number of loops between the set of pulleys 19 and 20. For example, if the initial counterbalancing force is determined by an initial elongation of the spring that is in the range of 15 cm, a stroke of 15 cm of the rod 11 and a number of five (5) pulleys per set would yield an additional spring elongation of 3 cm representing a difference of 20% in the counterbalancing force between the two extreme positions of the rod. The force adjustment device 17 comprises a lever 21 and a pulley 22. The second end of the coil spring 18 is connected to the force adjustment device 17 through a wire 23. Moving the lever 21 in direction 124 winds the wire 23 on a pulley 22 to extend the coil spring 18 by a maximum additional length of about 6 cm. providing adjustment up to about +40% with respect to the initial counterbalancing force. Of course, moving the lever 21 is a direction opposite to direction 124 will retract the coil spring 18 to reduce accordingly the counterbalancing force The force adjustment device 17 is so assembled to the tube 16 to have a high level of static friction to maintain the lever 21 at the set position despite the reaction force exerted by the spring 18 through the wire 23.

In operation, the user first adjusts the lateral position and the height of the graduated post 4 on the base 1 through the knob 3 so that his (her) arm lying on the rest member 13 is floating at the desired average working height within the work envelope. Moving the arm up or down within a range of 15 cm will only change the counterbalancing force by ±10% according to the previous example. Fine adjustment of the neutral vertical position is accomplished by moving the lever 21 up or down. The nominal horizontal distance between the base 1 and the centre of the work envelope is adjusted by manually sliding the sliding member 7 in or out.

The above described counterbalancing mechanism represents a simple, compact, reliable and low cost solution to produce a relatively constant counterbalancing force. Nevertheless, other types of known adjustable counterbalancing mechanisms such as spiral springs could be used to generate a relatively constant counterbalancing force over the stroke of the rod 11 without departing from the spirit of the present invention.

Figures 5, 6:
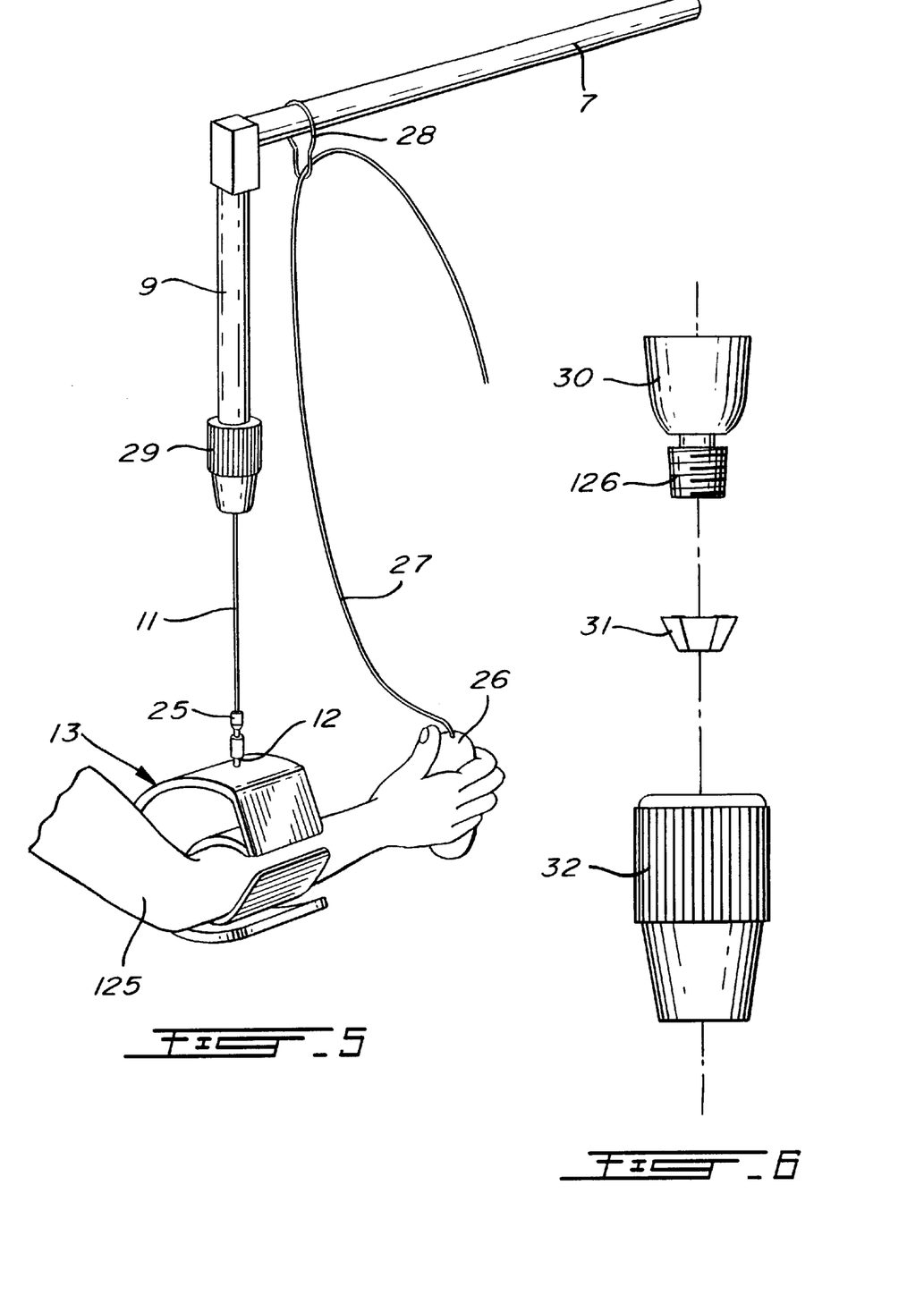
FIG. 5 is an enlarged isometric view of the fore-end of the overhead articulated arm support of FIG. 3, showing the operator's arm supported by an armrest, the probe and the probe cable in a typical position.
FIG. 6 is an enlarged assembly drawing of a friction coupling assembly of the overhead articulated arm support of FIG. 5.
Figure 9A:
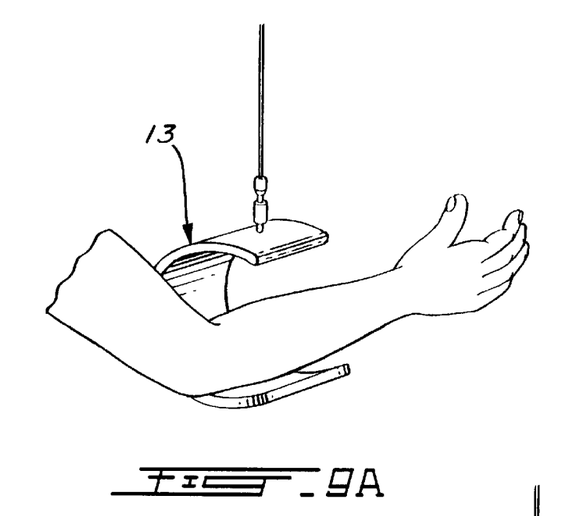
FIG. 9a illustrates an alternative embodiment of the armrest assembly.
Figure 9B:
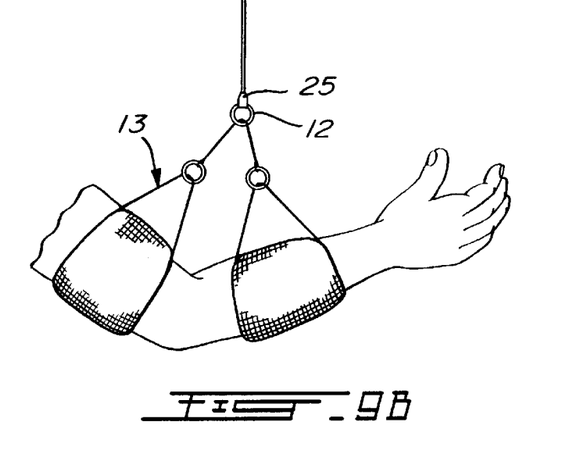
FIG. 9b illustrates another alternative embodiment of the armrest assembly.
Figure 9C:
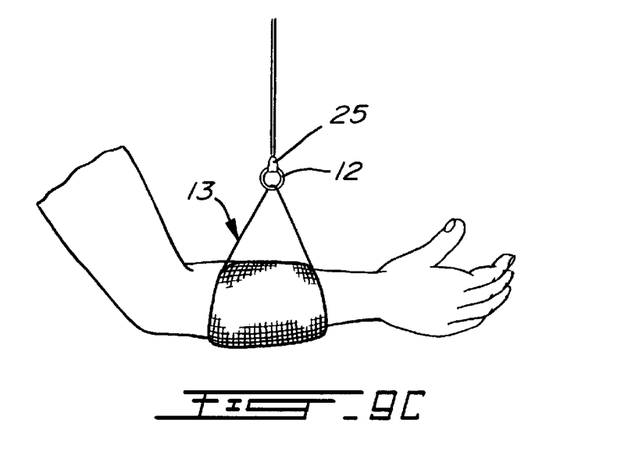
FIG. 9c illustrates a further alternative embodiment of the armrest assembly.

In FIG. 5, an operators arm 125 is shown in a working position, holding an ultrasonic probe 26 having a cable 27 supported by a cable supporting ring 28 to counterbalance its weight. The arm is directly supported on a rest member 13 usually under the forearm between the wrist and the elbow for maximum comfort and mobility. The rest assembly is removably connected to the lower part of the rod 11 by a quick-connect fastener 25. A "C"-shaped open type armrest 13 is represented in FIG. 5. However, alternate embodiments of the armrest 13 having one or more point of support as respectively shown in FIGS. 9a, 9b and 9c can be used according to the user's preferences. Of course, a further embodiment of armrest has been described with reference to FIGS. 1, 7 and 8.

FIG. 6 illustrates the details of the friction coupling 29. A connector 30 with a threaded portion 126 is fixed to the lower end of the tube 10. A frusto-conical friction ring 31 made of resilient material is sled on the rod 11 and is more or less compressed by screwing a torque knob 32 on the threaded portion 126 of connector 30. The degree of compression of the friction ring 31 will determine the level of resistance by friction to sliding of the rod 11 in the tube 10. It is also contemplated that asymmetrical friction devices providing resistance to the movement in only one direction could also be used, depending on the requirements of the intended application of the overhead articulated arm support Although the present invention has been described by means of preferred embodiments thereof, it is contemplated that various modifications may be made thereto without departing from the spirit and scope of the present invention. Accordingly, it is intended that the embodiments described be considered only as illustrative of the present invention and that the scope thereof should not be limited thereto but be determined by reference to the claims hereinafter provided and their equivalents.

For instance, it is contemplated that a version of the support without the base could be mounted on a workbench or wheelchair to accommodate usage for assembly operations or by a person with restrained mobility. Also, the detachable vertical assembly of the first preferred embodiment of the invention could be suspended to a ceiling mounted railing to provide similar benefits to the user.

It is also contemplated that the inventive preferred embodiment of the detachable armrest can be advantageously used in cooperation with other apparatus aiming at securing a member or other part of the human body in a definite position, limiting its axial movement.

What is claimed is:

1. A system for supporting a user's arm, comprising:
   an armrest for the user's arm; and
   a horizontally movable, armrest suspending and supporting structure comprising:
      a vertically movable member through which the armrest is suspended;
      a return-force producing assembly connected to the vertically movable member and comprising a resilient member through which an upward pulling force is applied to said vertically movable member; and
      a movement-resisting friction assembly connected to the vertically movable member and through which a friction force is applied to said vertically movable member;
   wherein the friction force is smaller than the upward pulling force but has an amplitude sufficient to add to the upward pulling force to counterbalance the weight of the user's arm within a given range of vertical arm positions and support the user's arm in a floatation-like mode within said given range of vertical arm positions.

2. A system as recited in claim 1, wherein:
   the vertically movable member comprises a wire; and
   the return-force producing assembly comprises:
      an elastic member having a first end fixedly connected to the horizontally movable structure, and a second end, wherein said elastic member constitutes said resilient member;
      a first set of laterally adjacent pulleys rotatively mounted on an axle itself fixedly mounted on the horizontally movable structure; and
      a second set of laterally adjacent rotative pulleys between the first set of pulleys and the second end of the elastic member;
   wherein the wire has a first end attached to the second end of the elastic member, is successively passed through the pulleys of the first and second sets to form a plurality of loops, and has finally its second end attached to the armrest.

3. A system as recited in claim 2 wherein:
   the second end of the wire is attached to the armrest through a generally vertical rod slidably mounted in a generally vertical tube of the horizontally movable structure; and
   the movement-resisting friction assembly comprises a friction element interposed between the generally vertical rod and the generally vertical tube.

4. A system as recited in claim 2 wherein:
   the second end of the wire is attached to the armrest through a generally vertical rod slidably mounted in a generally vertical tube of the horizontally movable structure; and
   the movement-resisting friction assembly comprises a friction element interposed between the generally vertical rod and the generally vertical tube.

5. A system as recited in claim 1, wherein the horizontally movable structure further comprises:
   a base member with a generally vertical tube;
   a generally vertical post slidably mounted in the generally vertical tube of the base member;
   a first arm pivotally mounted on the generally vertical post about a generally vertical pivot to move in a generally horizontal plane; and
   a second arm pivotally mounted on the first arm about a generally vertical pivot to move in a generally horizontal plane;
   wherein the armrest is suspended from the second arm.

6. A system as defined in claim 1, wherein the armrest comprises:
   a C-shaped shell having first and second ends;
   a lever pivotally mounted at the first end of the C-shaped shell and pivoting on said first end to close said C-shaped shell; and
   a flexible band having a first end attached to the lever and a second end attached to the second end of the C-shaped shell;
   wherein the flexible band is shorter than the C-shaped shell whereby, in operation, when the user's arm is placed on the flexible band, the lever is pulled and pivoted to close the C-shaped shell and surround the users arm with said flexible band.

7. An armrest as defined in claim 6, further comprising soft padding material between the C-shaped shell and the flexible band.

8. An armrest as defined in claim 6, wherein the first end of the flexible band is formed with a pocket to receive said lever.

9. An armrest as defined in claim 6, further comprising:
   a connecting rod for suspending the armrest; and
   a pivotal mechanism for connecting the C-shaped shell to the connecting rod, said pivotal mechanism defining a rotation axis and comprising a rotation-limiting arrangement.

10. A system for supporting a user's arm, comprising:
    an armrest for the users arm;
    a horizontally movable, armrest suspending and supporting structure comprising:
       a vertically movable member through which the armrest is suspended;
       a return-force producing assembly connected to the vertically movable member; and a movement-resisting assembly connected to the vertically movable member;

wherein;

the vertically movable member comprises a cable;

the return-force producing assembly comprises a first, spring-loaded reel on which a portion of said cable is wound; and the movement-resisting assembly comprises:

a second reel on which turns of said cable are wound, said second reel comprising a lateral face; and a friction disk applied to the lateral face of the second reel.

11. A system as recited in claim 10, wherein the cable is a substantially rigid cable whereby (a) the second reel is rotated as the cable is pulled downwardly to induce resistance to downward movement of said cable, and (b) the substantially rigid cable loses frictional contact with the second reel when no downward pulling force is applied to the substantially rigid cable to enable upward movement of said cable and rewinding thereof on the first reel substantially without resistance.

12. A system as recited in claim 10 wherein:

the second reel has two opposite lateral faces; and the movement-resisting assembly comprises:

two friction disks applied to the two lateral faces, respectively; and a pressure adjustment mechanism connected to the two friction disks and through which the level of pressure applied to the two lateral faces by the two friction disks, respectively, is adjusted.

13. An armrest suspending structure comprising:

a vertically movable member through which the armrest is suspended;

a return-force producing assembly connected to the vertically movable member and comprising a resilient member through which an upward pulling force is applied to said vertically movable member; and a movement-resisting friction assembly connected to the vertically movable member and through which a friction force is applied to said vertically movable member;

wherein the friction force is smaller than the upward pulling force but has an amplitude sufficient to add to the upward pulling force to counterbalance the weight of the user's arm within a given range of vertical arm positions and support the user's arm in a flotation-like mode within said given range of vertical arm positions.

14. A structure as recited in claim 13, wherein:

the vertically movable member comprises a wire; and the return-force producing assembly comprises;

an elastic member having a first end fixedly connected to the horizontally movable structure, and a second end, wherein said elastic member constitutes said resilient member;

a first set of laterally adjacent pulleys rotatively mounted on an axle itself fixedly mounted on the horizontally movable structure; and a second set of laterally adjacent rotative pulleys between the first set of pulleys and the second end of the elastic member;

wherein the wire has a first end attached to the second end of the elastic member, is successively passed through the pulleys of the first and second sets to form a plurality of loops, and has finally its second end attached to the armrest.

15. An armrest suspending structure comprising:

a vertically movable member through which the armrest is suspended;

a return-force producing assembly connected to the vertically movable member; and a movement-resisting assembly connected to the vertically movable member;

wherein;

the vertically movable member comprises a cable;

the return-force producing assembly comprises a first, spring-loaded reel on which a portion of said cable is wound;

the movement-resisting assembly comprises:

second reel on which turns of said cable are wound, said second reel comprising at least one lateral face; and at least one friction disk applied to the lateral face of the second reel.

16. A structure as recited in claim 15 wherein the cable is a substantially rigid cable whereby (a) the second reel is rotated as the cable is pulled downwardly to induce resistance to downward movement of said cable, and (b) the substantially rigid cable looses frictional contact with the second reel when no downward pulling force is applied to the substantially rigid cable to enable upward movement of said cable and rewinding thereof on the first reel substantially without resistance.

* * * * *